United States Patent [19]

Waller

[11] Patent Number: 4,806,674

[45] Date of Patent: Feb. 21, 1989

[54] PREPARATION OF URETHANES BY OXIDATIVE CARBONYLATION OF AMINES USING COPPER CARBOXYLATES AS OXIDANTS

[75] Inventor: Francis J. Waller, Wilmington, Del.

[73] Assignee: E. I. Du Pont De Nemours and Company, Wilmington, Del.

[21] Appl. No.: 821,324

[22] Filed: Jan. 27, 1986

Related U.S. Application Data

[63] Continuation-in-part of Ser. No. 703,425, Feb. 20, 1985, abandoned.

[51] Int. Cl.$^4$ ............................................. C07C 125/06
[52] U.S. Cl. .................................... 560/024; 560/115; 560/157; 560/025
[58] Field of Search ................. 560/024, 165, 157, 025

[56] References Cited

U.S. PATENT DOCUMENTS

| | | | |
|---|---|---|---|
| 3,405,156 | 10/1958 | Stern et al. | 260/453 |
| 3,641,092 | 2/1972 | Henry | 260/453 |
| 4,227,008 | 10/1980 | Miyata et al. | 560/25 |
| 4,251,667 | 2/1981 | Kesling, Jr. | 560/24 |
| 4,260,781 | 4/1981 | Harvey | 560/24 |
| 4,266,070 | 5/1981 | Moy | 560/24 |

FOREIGN PATENT DOCUMENTS

| | | | |
|---|---|---|---|
| 1192570 | 8/1985 | Canada | 260/468 |
| 54218 | 6/1982 | European Pat. Off. | 560/024 |
| 200556 | 11/1986 | European Pat. Off. | 560/024 |
| 0149552 | 8/1985 | Japan | 560/024 |

OTHER PUBLICATIONS

Durand, et al., *Tetrahedran Letters*, 28 (1969) 2329–2330.
Fukuoka, et al., *J. Chem. Soc., Chem. Comm.* (1984) 399–400.
Fukuoka, et al., *J. Org. Chem.*, 49 (1984), 1458–1460.
Narain, *Canadian Journal of Chemistry*, 44, (1966) 895.
Kokot, et al., *Inorganic Chemistry*, 3, (1964), 1306.
Alper, et al., *J. Chem. Soc., Chem. Commun.*, (1985) 1141.

*Primary Examiner*—Paul J. Killos

[57] ABSTRACT

A process for preparing urethanes by reacting a primary or secondary amine with carbon monoxide, an alcohol, a catalytic quantity of a compound or complex of palladium, platinum or rhodium and a stoichiometric quantity of a copper(II) salt of a monocarboxylic acid. When the amine is aromatic, the process is conducted in the presence of a selected Lewis base promoter and a compound or complex of palladium.

34 Claims, No Drawings

PREPARATION OF URETHANES BY OXIDATIVE CARBONYLATION OF AMINES USING COPPER CARBOXYLATES AS OXIDANTS

CROSS-REFERENCE TO RELATED APPLICATION

This is a continuation-in-part of copending patent application Ser. No. 703,425, filed on Feb. 20, 1985, now abandoned.

BACKGROUND OF THE INVENTION

1. Field of the Invention

This invention concerns an improved process for the preparation of urethanes (carbamates) by reacting a primary or secondary amine with carbon monoxide, an alcohol, an oxidant, and a catalyst.

2. References

U.S. Pat. No. 3,405,156 discloses a process for the production of isocyanates comprising reacting an amine with carbon monoxide and a platinum group metal including platinum, palladium, and rhodium. Regeneration of the platinum group metal is disclosed employing polyvalent metal compounds including halides and acetates of copper, mercury, cerium, iron, cobalt and the like, preferably cupric chloride and ferric chloride.

Durand et al., Tetrahedran Letters (1969) 28, 2329, and 2330, disclose the effect of various phosphines on selectivity in the carbonylation of amines to formamides and ureas catalyzed by rhodium complexes.

U.S. Pat. No. 3,641,092 discloses conversion of an organic amine to an isocyanate by reaction of the amine with carbon monoxide in contact with palladium chloride. The catalyst can be regenerated with oxygen or in admixture with copper chloride and oxygen.

U.S. Pat. No. 4,251,667 discloses the preparation of aromatic urethanes by reaction between aromatic amines, alcohols and carbon monoxide using copper salts, preferably copper halides, as catalysts. In a regenerating copper catalyst system, an oxygen-containing gas and a dehydrating agent are employed. Copper(II) acetate can be employed.

U.S. Pat. Nos. 4,260,781 and 4,266,070 disclose the preparation of carbamates in which an organic amine is contacted, in the substantial absence of reactive oxygen, with carbon monoxide, an alcohol, and a molar quantity of a Group VIII metal compound or complex or selected metal carbonyls.

U.S. Pat. No. 4,227,008 discloses that aromatic urethanes can be produced by interacting an aromatic primary amino compound having a nitro group, a nitroso group or a carbamate group, an organic compound having at least one hydroxyl group, and carbon monoxide in the presence of a catalytic system composed of a platinum group metal and/or a compound thereof serving as a catalyst and a Lewis acid and/or a compound thereof as promoter under high temperature and pressure. Examples of Lewis acids given include acetates among possible anions and copper among possible metals.

EP No. 71,835 discloses the preparation of a carbamate by reaction of a urea with carbon monoxide, an alcohol, molecular oxygen, a Group VIII metal catalyst, and a quinoid oxidizing agent, optionally in the presence of a metal redox compound such as copper(II) acetate.

Fukuoka et al., J. Chem. Soc., Chem. Commun. (1984), 399 and 400, describe the oxidative carbonylation of amines by carbon monoxide, oxygen and alcohols to give carbamates using a palladium and iodide ion catalyst system.

Fukuoka et al., J. Org. Chem. (1984) 49, 1458 to 1460, describe the oxidative carbonylation of amines by carbon monoxide, oxygen and alcohols to give carbamates using a platinum group metal and alkali metal halide or onium halide catalyst system.

Narain, Canadian Journal of Chemistry, 44, 895 (1966), describes the preparation of coordination complexes of copper(II) acetate, ammonia, aliphatic amines, and pyridine. For the copper(II) acetate amine complexes disclosed, the molar ratio of amine to copper(II) in the complexes is 2:1.

Kokot et al., Inorganic Chemistry, 3, 1306 (1964), describe the preparation of amine copper(II) complexes wherein the molar ratio of amine to copper(II) is 1:1.

SUMMARY OF THE INVENTION

This invention concerns a process for the preparation of urethanes which comprises reacting a primary or secondary amine, an alcohol, and carbon monoxide in the presence of a catalytic quantity of a compound or a complex of a metal selected from palladium, platinum and rhodium, and in the presence of a stoichiometric quantity of an oxidant selected from a copper(II) salt of a monocarboxylic acid having from 1 to 20 carbon atoms. When the amine is aromatic or aromatic heterocyclic, the metal compound or complex is rhodium trichloride, platinum(II) chloride, or a compound or complex of palladium. When the organic moiety of the amine is substituted, the substitutent is an alkyl, alkoxy, halo or aryl group and the number of such substituents is 1 or 2. In one embodiment of the invention, the amine is present as a copper carboxylate amine adduct. Novel adducts are also disclosed.

DETAILED DESCRIPTION OF THE INVENTION

The process of the invention is believed to proceed by the following overall pathway:

$$R(NHR^1)_n + nR^2OH)_q{}^4 + 2nCu(O_2CR^3)_2 + nCO$$
$$\rightarrow R(N(R^1)CO_2R^2)_n + 2nCu(O_2CR^3) + 2nR^3CO_2H$$

wherein:

R is selected from substituted or unsubstituted $C_1$ to $C_{20}$ alkyl, alkylene, cycloalkyl, cycloalkylene, aryl, alkaryl, aralkyl, and heterocycle-containing moiety;

$R^1$ is selected from hydrogen, $C_1$ to $C_6$ alkyl and $C_3$ to $C_6$ cycloalkyl;

n is an integer from 1 to 4;

$R^2$ is selected from substituted or unsubstituted $C_1$ to $C_{20}$ alkyl, cycloalkyl, and aralkyl;

$R^3$ is selected from substituted or unsubstituted $C_1$ to $C_{20}$ alkyl, cycloalkyl, aryl, alkaryl and aralkyl. The foregoing equations apply for when q is 1. The coefficient q can also be 2 or 3 in which cases the coefficients in the above equations require appropriate adjustment.

There are usually no more than about two substituents in any one of R, $R^2$, or $R^3$, preferably alkyl, alkoxy, halo or aryl. The terms "heterocycle-containing moiety" and "heterocyclic moiety" employed herein refer to moieties that contain an atom selected from the group oxygen, sulfur and nitrogen, preferably nitrogen.

In the process of this invention, reaction temperature and pressure usually are not critical; temperatures will usually be about 50° to 120° C. and pressures about 0.1 to 10.0 MPa. Preferred temperatures are about 65° to 115° C. and preferred pressures are about 4.0 MPa or lower. When the amine is aromatic and the catalyst is platinum(II) chloride, it is preferred to carry out the reaction at or near atmospheric pressure. The carbonylation process of this invention can be carried out in continuous, semi-continuous and batch operations. The type of reactor is not critical as long as it is able to withstand the temperatures and pressures involved. Pressure vessels of high tensile steel are typically used, either lined or unlined. Suitable reactor liners include nickel-based corrosion-resistant alloys (such as Hastelloy metals), stainless steel, tantalum, glass, and glazed ceramics.

Amines which can be employed in the process of the invention include any monofunctional or polyfunctional primary or secondary aliphatic, cycloaliphatic, aromatic or heterocyclic amine. By aliphatic amine is meant one in which the substituents on nitrogen are alkyl radicals or arylalkyl radicals, e.g., benzyl. The heterocyclic amine may contain an aromatic or aliphatic heterocyclic moiety. Preferably, the amine is a mono- or difunctional primary amine and has a maximum of 14 carbon atoms.

Particularly preferred amines are aliphatic amines, unsubstituted or alkyl-substituted anilines, and unsubstituted or alkyl-substituted benzylamines. Amines which can be employed in the carbonylation process include methylamine, n-butylamine, isobutylamine, tert-butylamine, n- and isopropylamine, hexylamine, octylamine, hexamethylenediamine, n-decylamine, cyclohexylamine, benzylamine, p-methylbenzylamine, p-ethylbenzylamine, aniline, the toluidines, the xylidines, toluenediamines, p-chloroaniline, 3,4-dichloroaniline, m-bromoaniline, methylene dianiline, α-naphthylamine, p-phenylenediamine, m-phenylenediamine, 3-aminopyridine, 1,4-diaminocyclohexane, 1,3-diaminocyclohexane, N-methylaniline, piperidine, dimethylamine, N-methylbutylamine, morpholine, thiomorpholine, and 2-thiophenemetylamine. Aniline and methylene dianiline are especially preferred.

Alcohols which can be employed in the process are mono-, di- or trihydric alcohols, preferably monohydric alcohols, wherein $R^2$ is an optionally substituted aliphatic, cycloaliphatic, or arylaliphatic group, preferably containing 1 to 20 carbon atoms and more preferably containing 1 to 6 carbon atoms. Alcohols which can be employed in the carbonylation process include methanol, ethanol, 1-propanol, 2-propanol, 1-butanol, 2-butanol, 1-pentanol, 1-hexanol, 1,6-hexanediol, 1,1,2,4-hexanetriol, glycerol, benzyl alcohol, cyclohexanol, lauryl alcohol, myristyl alcohol, stearyl alcohol, 1-eicosanol, and 1,4-butanediol. Methanol and ethanol are most preferred.

The equivalent ratio of alcohol to amine is not critical, but it is usually at least 1:1. It is preferred to employ excess alcohol as a solvent for the carbonylation reaction. When a higher molecular weight alcohol or primary amine is used, an additional solvent, e.g., hydrocarbons, nitriles, and tetramethylenesulfone, can be added to the reaction.

The compounds and complexes of metals that can be employed in the carbonylation process comprise members selected from the group consisting of compounds and complexes of palladium, platinum, and rhodium. Preferably the metal is palladium. It is preferred that the metal is at least in a divalent state, i.e., a valence state of +2 or higher. The compound or complex containing the designated metals can be inorganic or organic, and mixed salts of the metals can also be used. Suitable inorganic salts include chlorides, bromides, iodides, sulfates, nitrates, silicates, and the like. Suitable organic salts include carboxylate salts such as acetate, propionate, butyrate, and trifluoroacetate. Preferred complexes of metal ion salts which can be employed include phosphine and arsine complexes. Compounds and complexes which can be employed include $Pd(O_2CCH_3)$, $PdCl_2$, $PdBr_2$, $PdI_2$, $Pd(O_2CCF_3)_2$, $PtCl_2$, $PtI_2$, $RhCl_3 \cdot XH_2$, $[(C_6H_5)_3P]_2PdCl_2$, $[(C_6H_5)_3As]_2PdCl_2$, $[(C_6H_{11})_3P]_2PdCl_2$, and $[(C_6H_5)_3P]_4Pd$.

The metal is employed in a catalytic quantity based on amine, i.e., the amine groups to metal molar ratio will range from about 5:1 to 50:1, and preferably from about 8:1 to 40:1. When an aromatic or aromatic heterocyclic amine is employed as a reactant, the metal will be selected from rhodium trichloride, platinum(II) chloride, or a compound or complex of palladium.

The stoichiometric oxidants which can be employed are selected from copper(II) salts of monocarboxylic acids. Particularly preferred are salts of carboxylic acids which contain 1 to 6 carbon atoms. Examples of acids which can be employed in their copper(II) salt form include formic, acetic, propionic, butyric, isobutyric, cyclohexanecarboxylic, valeric, hexanoic, decanoic, dodecanoic, chloroacetic, benzoic, p-toluic, phenylacetic, and methoxyacetic. The stoichiometric oxidant is usually employed in a molar ratio of about 200:1 to 2:1 based on the metal, and preferably about 100:1 to 2:1.

It is not necessary that the copper(II) carboxylate be added directly to the reaction mixture. For example, when copper(II) chloride and the sodium salt of a carboxylic acid, e.g., sodium acetate or sodium butyrate, are charged to the reaction vessel, the corresponding copper(II) carboxylate, e.g., copper(II) acetate or copper(II) butyrate, are formed in situ in the reaction mixture. Preferably, the copper(II) salt is dried before use to remove any water of crystallization and obtain substantially anhydrous salt.

When an aromatic amine is employed as the reactant with a palladium metal compound or complex, addition of a selected Lewis base to the reaction increases the reaction rate as measured by catalyst turnover rate and increases the selectivity of the reaction based on the alcohol reactant. For example, in the oxidative carbonylation of aniline with ethanol as the alcohol, significant amounts of byproducts, diethyl carbonate and diethyl oxalate, are normally formed. However, when a Lewis base is added to the reaction mixture, the selectivity of ethanol conversion to carbamate is increased significantly.

Lewis bases which can be employed as promoters include aliphatic, aromatic, and heterocyclic tertiary amines and phosphines. They include triethylamine, tri-n-propylamine, tri-n-butylamine, triphenylamine, tribenzylamine, pyridine, 2-, 3-, and 4-methylpyridine, 2-ethylpyridine, 2,6-dimethylpyridine, 2,5-dimethylpyridine, 3,4-dimethylpyridine, 2,2,-dipyridyl, 2,2'-biquinoline, poly(2-vinylpyridine), poly(4-vinylpyridine), triphenylphosphine, and tri(o-tolyl)phosphine. The Lewis base is employed in a molar ratio of about 2:1 to 100:1, preferably about 4:1 to 25:1, based on the metal. Preferred Lewis bases are pyridine and methyl-substituted pyridines.

In another embodiment of the process of the invention the amine can be employed in the process of the invention in the form of a copper carboxylate amine adduct. Preferably, the adduct has the formula, [Cu(O$_2$CR$^3$)$_2$]$_m$.$_{RNHR}$$^1$, wherein R, R$^1$ and R$^3$ are the same as earlier defined and m is 0.5, 1 or 2. Preferably R$^1$ is hydrogen, R$^3$ is methyl and R is an alkyl or aryl group. When R is alkyl, it is preferably n-butyl and when R is aryl, it is preferably phenyl. Adducts wherein m is 0.5 or 1 can be made by procedures known in the art, e.g., by refluxing the amine and the copper carboxylate in a medium such as acetonitrile to obtain a slurry from which the liquid is removed by evaporation to yield solid that is then dried at about 40° C. to give the adduct. Adducts wherein m is 2 can be prepared by a similar procedure; however, the solid removed from the slurry is heated at a temperature of from about 60° C. to about 120° C., preferably at about 110° C. In this embodiment the alcohol and compound or complex of palladium, platinum or rhodium are employed as previously set forth herein. Preferably, the total amount of oxidant, including that contributed by the copper carboxylate amine adduct, is sufficient to give a molar ratio of copper to amine reactant of at least about 2:1.

To regenerate the stoichiometric copper(II) carboxylate oxidant, it is desirable to carry out the carbonylation process in the presence of an oxidizing agent e.g., oxygen. This regeneration process is useful when an aliphatic amine or methylene dianiline is employed as the substrate. To accomplish this objective, a mixture of carbon monoxide and oxygen can be employed in the carbonylation (see Examples 29, 30 and 65). If oxygen or air is employed in the carbonylation process, it is preferable that the oxygen concentration in the reaction zone at any given time be less than the explosive range of oxygen in carbon monoxide, i.e., less than about 6.0 volume percent.

Alternatively, the reduced copper carboxylate can be removed from the process reactor and the copper(II) carboxylate regenerated separately as a side stream when the carbonylation is carried out in a continuous process. Separate regeneration is useful with any type of amine substrate. Separate regeneration of the copper(II) carboxylate is illustrated by Examples 1 and 2.

In the carbonylation process, the order of mixing of the reactants is not critical and can be varied within the limitations of the equipment employed. A simple procedure is to charge the amine reactant, the alcohol, the metal compound or complex, copper(II) carboxylate, Lewis base, if one is used, and any added solvent to the reaction vessel, introduce the carbon monoxide, and then heat the mixture to the desired temperature and pressure to effect the carbonylation reaction. It is preferred to add the amine reactant in increments (see Example 62). The total pressure can be controlled by the amount of carbon monoxide employed and the free space in the reaction vessel. As the reaction progresses, an additional quantity of carbon monoxide can be added to the reactor, either intermittently or continuously, if desired.

The reaction time will be dependent upon the nature of the amine, the concentration of the catalyst and oxidant, temperature and pressure employed, the type of equipment used, and whether the process is continuous or batch. After the carbonylation reaction is complete, the reaction product can be treated by conventional procedures including filtration, distillation, or other suitable separation techniques, to effect separation of the urethane from unreacted starting material, solvent, by-product and educed catalyst.

The invention is characterized by use of a catalytic quantity of noble metal and a stoichiometric quantity of a copper(II) carboxylate oxidant. The process is characterized further by good product yields, and good catalyst turnover and turnover rate. In general, it has been found that catalyst turnover and turnover rate each exceeds 2.0 and product yields with aliphatic amines exceed about 65 percent.

Product yield is defined as the mols of product urethane formed per mol of amine charged, in percent. Turnover is defined as the mols of product urethane formed per mol of metal catalyst. Turnover rate is defined as the mols of product urethane formed per mol of metal catalyst per hr. Selectivity to urethane, based on the alcohol, is defined by the following equation:

$$\text{Selectivity} = \frac{\text{mols urethane}}{\Sigma[\text{mols urethane} + 2 \text{ (mols alkyl carbonate} + 2 \text{ (mols alkyl oxalate)}]}.$$

The invention is further illustrated by the following Examples. In the following Procedure and in the Examples all parts and percentages are by weight and all degrees are Celsius unless otherwise noted. Preferred embodiments of this invention are represented by Examples 1, 29, 38 and 65.

GENERAL CARBONYLATION PROCEDURE

The alcohol, amine, metal compound or complex, and copper(II) salt were charged at atmospheric pressure to a glass round-bottomed flask equipped with a reflux condenser and a glass tube below the surface of the liquid for introducing carbon monoxide. The copper(II) salt was previously dried at 110° in a vacuum oven for several hours to remove water and obtain the anhydrous salt. The resulting reaction mixture was heated to reflux and carbon monoxide was slowly bubbled through the solution for the required time. At the end of the reaction, the solution was cooled, and a weighed amount of internal standard, monochlorobenzene, was added. The reaction mixture was analyzed by GC using a 3.05 m×0.32 cm (10'×⅛") stainless steel column packed with 10% methylsilicone oil (SE-30) on 80/100 mesh diatomaceous earth. Molar response factors were referenced against monochlorobenzene.

The reactions performed at elevated carbon monoxide pressure were carried out in a 90 mL glass Fischer-Porter tube. The Fischer-Porter tube was charged with the reactants, as described. The tube was connected to a valve assembly and pressurized with carbon monoxide. The tube was inserted into an oil bath or hot air at the reaction temperature, and the carbon monoxide pressure was increased to the desired total pressure. The product was analyzed by GC as described.

EXAMPLE 1

A mixture of 20 mL of ethanol, 5.4 mmol of n-butylamine, 0.313 mmol of palladium acetate, and 11.0 mmol of copper(II) acetate was heated under reflux for 70 min while carbon monoxide was bubbled through the solution. GC analysis of the reaction mixture showed the presence of 5.30 mmol (96.7% yield) of ethyl N-n-butylcarbamate. Volatiles were removed at reduced pressure and the residue, 2.5 g, was added to 100 mL of acetic acid to form a solution which was then heated to reflux for about 3 hrs while air was bubbled through it. The resulting blue solution was cooled and then was concentrated at reduced pressure to leave 1.97 g of a mixture of solid reoxidized copper(II) acetate and palladium and-/or palladium acetate.

EXAMPLE 2

A mixture of 20 mL of ethanol, 2.74 mmol of n-butylamine and the reoxidized copper acetate/palladium acetate mixture recovered from Example 1 (1.97 g) was treated with carbon monoxide by the general procedure for 70 min. The yield of ethyl N-n-butylcarbamate was 100%.

EXAMPLE 3

A mixture of 10 mL of ethanol, 2.74 mmol of n-butylamine, 0.313 mmol of palladium acetate, and 3.29 mmol of copper(II) acetate was heated under reflux for 70 min while carbon monoxide was bubbled through the mixture. GC analysis of the resulting reaction mixture showed a 58.8% yield of ethyl N-n-butylcarbamate (theoretical yield of 60.2% based on copper(II) acetate) with a turnover of 5.1. In a comparative experiment, no product was obtained in the absence of palladium acetate (6.54 mmol of copper(II) acetate and 20 mL of ethanol were employed in the comparative experiment).

EXAMPLES 4 to 8

Summarized in Table 1 are the results of the oxidative carbonylation of n-butylamine with various copper(II) carboxylates to give ethyl N-n-butylcarbamate. In each Example, 2.74 mmol of n-butylamine, 0.313 mmol of palladium acetate (0.398 mmol of palladium chloride in Example 8), the designated amount of copper(II) carboxylate, and 20 mL of ethanol were heated under reflux for 70 min (100 min in Example 4) while carbon monoxide was bubbled through the solution.

TABLE 1

| Example | Copper(II) Carboxylate, mmol | Percent Yield | Turnover |
|---|---|---|---|
| 4 | (i-$C_3H_7CO_2$)$_2$Cu, 6.30 | 65.0 | 5.7 |
| 5 | (n-$C_4H_9CO_2$)$_2$Cu, 6.65 | 85.0 | 7.4 |
| 6 | ($C_6H_5CH_2CO_2$)$_2$Cu, 6.54 | 80.7 | 7.1 |
| 7 | ($CH_3OCH_2CO_2$)$_2$Cu, 7.85 | 33.2 | 2.9 |
| 8 | ($ClCH_2CO_2$)$_2$Cu, 6.40 | 86.1 | 5.9 |

EXAMPLES 9 to 13

These Examples demonstrate the use of various metal catalysts to effect oxidative carbonylation of n-butylamine, Examples 9 to 11, to give ethyl N-n-butylcarbamate or cyclohexylamine, Examples 12 and 13, to give ethyl N-cyclohexylcarbamate. Using the general carbonylation procedure, a mixture of 2.74 mmols of amine, the designated amount of metal compound, and 6.54 mmol of copper(II) acetate in 20 mL of ethanol was heated under reflux for 70 min while carbon monoxide was bubbled through the mixture. The results are summarized in Table 2.

TABLE 2

| Example | Metal Compound, mmol | Percent Yield | Turnover |
|---|---|---|---|
| 9 | $PdCl_2$, 0.341 | 92.3 | 7.4 |
| 10 | $PdI_2$, 0.306 | 75.9 | 6.8 |
| 11 | Pd($O_2CCF_3$)$_2$, 0.120 | 95.2 | 21.8 |
| 12 | $RhCl_3 \cdot XH_2O$, 0.305 | 95.9 | 8.6 |
| 13 | $PtCl_2$, 0.313 | 27.7 | 2.4 |

EXAMPLE 14

A Fischer-Porter tube was charged with p-methylbenzylamine (5.45 mmol), ethanol (40 mL), palladium acetate (0.536 mmol), and copper(II) acetate (13.08 mmols), charged with carbon monoxide, and heated at 78° and 80 psi (0.55 MPa) carbon monoxide pressure for 120 min. GC analysis of the product showed a yield of 78.9% ethyl N-p-methylbenzylcarbamate with a turnover of 8.0.

EXAMPLES 15 to 19

These Examples demonstrate in situ formation of the copper(II) carboxylate oxidant. The reactions were carried out by the general carbonylation procedure using 2.74 mmol of n-butylamine, 20 mL of ethanol (methanol in Example 18) and the designated metal compounds and oxidants at reflux for 70 min. The yields of ethyl N-n-butylcarbamate (methyl N-n-butylcarbamate in Example 18) are summarized in Table 3.

TABLE 3

| Example | Metal Compound (mmol) | Cu(II) Oxidant mmol | Percent Yield | Turnover |
|---|---|---|---|---|
| 15 | Pd($O_2CCH_3$)$_2$, 0.313 | $CuCl_2$, 6.72 Na($O_2CCH_3$), 3.66 | 50.7 | 4.4 |
| 16 | $PdCl_2$, 0.398 | $CuCl_2$, 6.72 Na($O_2CCH_3$), 7.32 | 84.3 | 5.8 |
| 17 | $PdCl_2$, 0.398 | $CuCl_2$, 6.72 Na($O_2CC_3H_7$), 7.27 | 100 | 6.9 |
| 18 | $PdCl_2$, 0.398 | $CuCl_2$, 6.72 Na($O_2CC_3H_7$), 7.27 | 99.6 | 6.9 |
| 19 | Pd($O_2CCH_3$)$_2$, 0.313 | $CuCl_2$, 6.57 $CH_3CO_2H$, 3.33 | 24.8 | 2.2 |

EXAMPLES 20 to 27

These Examples demonstrate the use of phosphine and arsine complexes of palladium as the catalyst for the oxidative carbonylation reaction. The reactions were carried out at the designated pressure and temperature by the general carbonylation procedure using either Procedure A or Procedure B, as follows.

Procedure A Reactants, 2.74 mmol of n-butylamine, 20 mL of ethanol, 6.59 mmol of copper(II) acetate; metal complex as designated; reaction time, 70 min.

Procedure B Reactants, 5.48 mmol of n-butylamine, 40 mL of ethanol, 13.18 mmol of copper(II) acetate; metal complex as designated; reaction time, 120 min.

The results and the yields of the product, ethyl N-n-butylcarbamate, are summarized in Table 4.

TABLE 4

| Ex. | Metal Complex, mmol | Reaction Pressure, kPa | Reaction Temp. °C. | Percent Yield | Turnover |
|---|---|---|---|---|---|
| 20 | [($C_6H_5$)$_3$P]$_2$PdCl$_2$, 0.286 | 0.10 | 78 | 97.4 | 9.3 |
| 21 | [($C_6H_5$)$_3$As]$_2$PdCl$_2$, 0.292 | 0.10 | 78 | 77.4 | 7.3 |
| 22 | [($C_6H_5$)$_3$P]$_2$PdCl$_2$ 0.571 | 0.41 | 85 | 58.8 | 5.6 |
| 23 | [($C_6H_5$)$_3$P]$_2$PdCl$_2$, 0.571 | 0.83 | 85 | 99.5 | 9.5 |
| 24 | [($C_6H_5$)$_3$P]$_2$PdCl$_2$, 0.286 | 0.83 | 80 | 77.2 | 14.8 |
| 25 | [($C_6H_5$)$_3$P]$_2$PdCl$_2$, 0.286 | 0.41 | 80 | 68.2 | 13.1 |
| 26 | [($C_6H_5$)$_3$P]$_2$PdCl$_2$, 0.286 | 0.83 | 60 | 89.2 | 17.1 |

TABLE 4-continued

| Ex. | Metal Complex, mmol | Reaction Pressure, kPa | Reaction Temp. °C. | Percent Yield | Turnover |
|---|---|---|---|---|---|
| 27 | [(C6H5)3P]2PdCl2, 0.286 | 0.41 | 60 | 94.2 | 18.0 |

EXAMPLE 28

Using the general carbonylation procedure, a mixture of 2.69 mmol of aniline, 20 mL of ethanol, 0.286 mmol of tetrakis(triphenylphosphione)palladium, and 6.59 mmol of copper(II) actate was heated under reflux at atmospheric pressure (0.10 MPa) for 70 min while carbon monomixde was bubbled through the mixture. A 74.4% yield of ethyl N-phenylcarbamate was obtained with a turnover of 7.0.

EXAMPLES 29 to 30

A mixture of 12.3 mmol of n-butylamine, 30 mL of ethanol, 0.446 mmol of palladium acetate, and 6.59 mmol of copper(II) acetate was charged to a 330 mL Hastelloy C pressure vessel, the vessel was charged with a gaseous mixture of 3 volume percent oxygen in carbon monoxide, and the vessel was heated at 80° for 120 min at a total pressure of 300 psi (2.07 MPa) (Example 29) or 1300 psi (8.96 MPa) (Example 30). The yield of ethyl N-n-butylcarbamate based on copper(II) acetate was 185% (based on reoxidized copper(II) acetate) in Example 29 and 82.5% in Example 30. Example 29 shows that the spent copper(I) acetate is reoxidized in situ to active copper(II) acetate by the oxygen present in the reaction mixture. A comparison of Examples 29 and 30 suggests that reoxidation is favored at lower pressure.

EXAMPLES 31 to 53

These Examples illustrate the use of Lewis base promoters in the oxidative carbonylation of aniline. Reactions were carried out by the general carbonylation procedure at atmospheric pressure using 2.15 mmol of aniline, 6.59 mmol of copper(II) acetate, 30 mL of ethanol, and the designated amounts of palladium(II) acetate catalyst and Lewis base promoter at reflux (78°) for 35 min. The results are summarized in Table 5.

TABLE 5

| Example | Pd(O2CCH3)2, mmol | Lewis Base, mmol | Lewis Base/ Pd(O2CCH3)2 | Selectivity | Turnover Rate |
|---|---|---|---|---|---|
| 31 | 0.089 | — | — | 0.33 | 10.1 |
| 32 | 0.179 | — | — | 0.30 | 7.5 |
| 33 | 0.089 | (C2H5)3N 0.99 | 11.1 | 0.41 | 14.3 |
| 34 | 0.089 | (C2H5)3N 1.98 | 22.2 | 0.56 | 20.6 |
| 35 | 0.089 | (C2H5)3N 3.96 | 44.4 | 0.60 | 30.2 |
| 36 | 0.089 | (C2H5)3N 5.94 | 66.7 | 0.48 | 17.1 |
| 37 | 0.179 | Pyridine 0.77 | 4.3 | 0.54 | 5.1 |
| 38 | 0.179 | Pyridine 3.79 | 21.2 | 0.88 | 8.8 |
| 39 | 0.089 | Pyridine 3.79 | 42.6 | 0.84 | 16.8 |
| 40 | 0.179 | Triphenylamine 1.63 | 9.1 | 0.37 | 5.5 |
| 41 | 0.179 | Tribenzylamine 0.70 | 3.9 | 0.49 | 5.9 |
| 42 | 0.179 | 4-Picoline 1.94 | 10.8 | 0.69 | 6.7 |
| 43 | 0.179 | 2-Picoline 3.76 | 21.0 | 0.80 | 4.8 |
| 44 | 0.179 | 2,6-Dimethyl pyridine 2.80 | 15.6 | 0.70 | 9.0 |
| 45 | 0.179 | 2,2'-Dipyridyl 0.97 | 5.4 | 0.70 | 10.6 |
| 46 | 0.179 | 2-2'-Biquinoline 1.88 | 10.5 | 0.42 | 9.6 |
| 47 | 0.179 | Poly-(4-vinylpyridine) 2.86 | 15.9 | 0.44 | 8.3 |
| 48 | 0.179 | Poly-(2-vinylpyridine) 2.86 | 15.9 | 0.76 | 3.9 |
| 49 | (1) | Triphenylphosphine 1.53 | 8.2 | 0.69 | 7.0 |
| 50[2] | 0.179 | — | — | 0.73[3] | 6.4 |
| 51[2] | 0.179 | Pyridine 3.85 | 21.5 | 1.26[3] | 12.1 |
| 52 | (4) | — | — | 0.46 | 6.4 |
| 53 | (4) | 2,2'-Dipyridyl | 4.8 | 0.66 | 8.9 |

TABLE 5-continued

| Example | Pd(O$_2$CCH$_3$)$_2$, mmol | Lewis Base, mmol | Lewis Base/ Pd(O$_2$CCH$_3$)$_2$ | Selectivity | Turnover Rate |
|---|---|---|---|---|---|
| | | | 0.90 | | |

[1] Palladium acetate was replaced with 0.186 mmol of [(C$_6$H$_5$)$_3$P]$_2$PdCl$_2$, and the reaction time was 70 min.
[2] Ethanol was replaced with 30 mL of methanol, and the reaction temperature was 65°.
[3] Mmol of methyl N—phenylcarbamate formed.
[4] Palladium acetate was replaced with 0.184 mmol of (2,2'-dipyridyl)palladium acetate.

EXAMPLE 54

This Example was carried out by the general procedure of Examples 31 to 53 (no Lewis base promoter was employed) except that the palladium acetate was replaced with 0.165 mmol of rhodium(III) chloride hydrate (42.4% rhodium). A selectivity to urethane of greater than 0.98 was obtained at a turnover of 6.3.

EXAMPLE 55

A Fischer-Porter tube was charged with aniline (2.15 mmol), ethanol (30 mL), rhodium trichloride hydrate (0.122 mmol), and copper(II) acetate (6.59 mmol), charged with a gaseous mixture of 3 volume percent oxygen in carbon monoxide, and heated at 85° and 1074 psi (7.4 MPa) carbon monoxide pressure for 15 min. GC analysis of the product showed a yield of 31% ethyl N-phenylcarbamate with a turnover of 5.5.

COMPARATIVE EXAMPLES A to F

These Comparative Examples show that copper(II), cobalt(II), and ferric(III) chlorides, and cobalt(II), and ferric(III) acetates do not serve as stoichiometric oxidants for reduced metal catalysts in the oxidation carbonylation reaction since the turnovers observed are less than 2. Reactions were carried out under reflux at atmospheric pressure by the general carbonylation procedure using 2.74 mmols of n-butylamine, 20 mL of ethanol, 0.341 mmol of palladium chloride and the designated oxidant. Results are summarized in Table 6.

TABLE 6

| Ex. | Oxidant Candidates, mmol | Reaction Time, min | Percent Yield | Turnover |
|---|---|---|---|---|
| A | CuCl$_2$, 6.57 | 70 | 10.9 | 0.87 |
| B | CuCl$_2$, 6.57 | 150 | 1.4 | 0.11 |
| C | CoCl$_2$, 6.59 | 150 | 9.1 | 0.73 |
| D | Co(O$_2$CCH$_3$)$_2$, 6.78 | 150 | 5.2 | 0.42 |
| E | FeCl$_3$, 6.78 | 150 | 0 | — |
| F | FeCl$_3$, 6.78 and Na(O$_2$CCH$_3$), 7.32 | 70 | 1.8 | 0.15 |

EXAMPLE 56

Preparation of Cu[OOCCH$_3$]$_2$[CH$_3$CH$_2$CH$_2$CH$_2$NH$_2$]$_{0.5}$

A round bottom flask was charged with 50 mL of acetonitrile, 13.2 mmol of Cu[OOCCH$_3$]$^2$ and 30.1 mmol of n-butylamine. After refluxing the resulting slurry for five hours, the slurry was cooled and then evaporated down to a solid. The solid was washed with benzene or cyclohexane to remove excess n-butylamine. The resulting adduct was dried in a vacuum oven for three hours at 110° C. The dried product gave the following elemental analysis.
Found: Cu, 28.53; C, 33.61; H, 5.53; N, 3.60. Theory: Cu, 29.12; C, 33.02; H, 5.31; N, 3.21.

COMPARATIVE EXAMPLE G

A round bottom flask was charged with 50 mL of acetonitrile, 13.2 mmol of Cu[OOCCH$_3$]$_2$ and 30.1 mmol of n-butylamine. After refluxing the resulting slurry for six hours, the slurry was cooled and then evaporated down to a solid. The solid was washed with benzene or cyclohexane to remove excess n-butylamine. The resulting adduct was dried in a vacuum oven for three-four hours at 40° C. The elemental analysis indicated Cu(OOCCH$_3$)$_2$[CH$_3$CH$_2$CH$_2$CH$_2$NH$_2$]$_2$ as the composition of the complex.
Found: Cu, 19.92; C, 43.83; H, 8.51; N, 8.52. Theory: Cu, 19.38; C, 43.95; H, 8.61; N, 8.54.

COMPARATIVE EXAMPLE H

A round bottom flask was charged with 50 mL of benzene, 13.2 mmol of Cu[OOCCH$_3$]$_2$ and 30.1 mmol of n-butylamine. After refluxing the resulting slurry for six hours, the slurry was cooled and then evaporated down to a solid. The solid was washed with benzene or cyclohexane to remove excess n-butylamine. The resulting adduct was dried in a vacuum oven for three-four hours at 40° C. The elemental analysis indicated Cu(OOCCH$_3$)$_2$[CH$_3$CH$_2$CH$_2$CH$_2$NH$_2$]$_2$ as the composition of the complex.
Found: Cu, 19.78; C, 43.81; H, 8.55; N, 8.54. Theory: Cu, 19.38; C, 43.95; H, 8.61; N, 8.54.

EXAMPLE 57

Preparation of Cu[OOCCH$_3$]$_2$[C$_6$H$_5$NH$_2$]$_{0.5}$

A round bottom flask was charged with 50 mL of acetonitrile, 13.2 mmol of Cu[OOCCH$_3$]$_2$ and 26.9 mmol of aniline. After refluxing the resulting slurry for five hours, the slurry was cooled and then evaporated down to a solid. The solid was washed with benzene or cyclohexane to remove excess aniline. The resulting adduct was dried in a vacuum oven for three hours at 110° C. The dried product gave the following elemental analysis:
Found: Cu, 27.00; C, 36.46; H, 4.11; N, 3.44. Theory: Cu, 27.85; C, 36.84; H, 4.19; N, 3.06.

COMPARATIVE EXAMPLE I

A round bottom flask was charged with 50 mL of benzene, 13.2 mmol of Cu[OOCCH$_3$]$_2$ and 26.9 mmol of aniline. After refluxing the resulting slurry for five hours, the slurry was cooled and then evaporated down to a solid. The solid was washed with benzene or cyclohexane to remove excess aniline. The resulting adduct was dried in a vacuum oven for three-four hours at 40° C. The elemental analysis indicated Cu[OOCCH$_3$]$_2$C$_6$H$_5$NH$_2$ as the composition of the complex.
Found: Cu, 23.53; C, 44.43; H, 4.87; N, 4.98. Theory: Cu, 23.13; C, 43.71; H, 4.77; N, 5.09.

COMPARATIVE EXAMPLE K

A round bottom flask was charged with 50 mL of benzene, 5.0 mmol of Cu[OOCCH$_2$CH$_2$CH$_3$]$_2$ (prepared by reacting copper carbonate with CH$_3$CH$_2$CH$_2$COOH in refluxing acetonitrile) and 10.8 mmol of aniline. After refluxing the resulting slurry for six hours, the slurry was cooled and then evaporated down to a solid. The solid was washed with benzene or cyclohexane to remove excess aniline. The resulting adduct was dried in a vacuum oven for four hours at 40° C. The elemental analysis indicated Cu[OOCCH$_2$CH$_2$CH$_3$]$_2$C$_6$H$_5$NH$_2$ as the composition of the complex.

Found: Cu, 20.04; C, 50.78; H, 6.30; N, 4.37. Theory: Cu, 19.21; C, 50.82; H, 6.39; N, 4.23.

COMPARATIVE EXAMPLE J

A round bottom flask was charged with 50 mL of acetonitrile, 9.7 mmol of Cu[OOCH]$_2$ (prepared by reacting copper carbonate with HCOOH in refluxing acetonitrile) and 19.4 mmol of aniline. After refluxing the resulting slurry for six hours, the slurry was cooled and then evaporated down to a solid. The solid was washed with benzene or cyclohexane to remove excess aniline. The resulting adduct was dried in a vacuum oven for three hours at 40° C. The elemental analysis indicated Cu[OOCH]$_2$C$_6$H$_5$NH$_2$ as the composition of the complex.

Found: Cu, 24.69; C, 39.08; H, 4.03; N, 6.02. Theory: Cu, 25.76; C, 38.95; H, 3.68; N, 5.68.

EXAMPLE 58

Reaction with Cu[OOCCH$_3$]$_2$[CH$_3$CH$_2$CH$_2$CH$_2$NH$_2$]$_2$

A mixture of 30 mL of ethanol, 2.44 mmol of Cu[OOCCH$_3$]$_2$[CH$_3$CH$_2$CH$_2$CH$_2$NH$_2$]$_2$, 0.179 mmol of Pd[OOCCH$_3$]$_2$, 3.79 mmol of pyridine and 7.69 mmol of Cu[OOCCH$_3$]$_2$ was heated under reflux for 24 minutes while carbon monoxide was bubbled through the mixture. GC analysis of the resulting reaction mixture showed the presence of 3.24 mmol of ethyl N-n-butylcarbamate. The turnover rate [TOR] of the palladium was 45.3 hr$^{-1}$.

EXAMPLE 59

Reaction with Cu[OOCCH$_3$]$_2$[CH$_3$CH$_2$CH$_2$CH$_2$NH$_2$]$_{0.5}$

A mixture of 30 mL of ethanol, 3.66 mmol of Cu[OOCCH$_3$]$_2$[CH$_3$CH$_2$CH$_2$CH$_2$NH$_2$]$_{0.5}$, 0.134 mmol of Pd[OOCCH$_3$]$_2$, 3.79 mmol of pyridine and 7.69 mmol of Cu[OOCCH$_3$]$_2$ was heated under reflux for 24 minutes while carbon monoxide was bubbled through the mixture. GC analysis of the resulting mixture showed the presence of 1.19 mmol of ethyl N-n-butylcarbamate. The TOR of the palladium was 22.2 hr$^{-1}$.

EXAMPLE 60

Reaction with Cu[OOCCH$_3$]$_2$C$_6$H$_5$NH$_2$

A mixture of 30 mL of methanol, 2.55 mmol of Cu[OOCCH$_3$]$_2$C$_6$H$_5$NH$_2$, 0.179 mmol of Pd[OOCCH$_3$]$_2$, 3.79 mmol of pyridine and 5.49 mmol of Cu[OOCCH$_3$]$_2$ was heated under reflux for 24 minutes while carbon monoxide was bubbled through the mixture. GC analysis of the resulting reaction mixture showed the presence of 1.48 mmol of methyl phenylcarbamate. The TOR of the palladium was 20.7 hr$^{-1}$.

EXAMPLE 61

Reaction with Cu[OOCCH$_2$CH$_2$CH$_3$]$_2$C$_6$H$_5$NH$_2$

A mixture of 30 mL of methanol, 1.81 mmol of Cu[OOCCH$_2$CH$_2$CH$_3$]$_2$C$_6$H$_5$NH$_2$, 0.134 mmol of Pd[OOCCH$_3$]$_2$, 3.79 mmol of pyridine and 5.49 mmol of Cu[OOCCH$_3$]$_2$ was heated under reflux for 24 minutes while carbon monoxide was bubbled through the mixture. GC analysis of the resulting reaction mixture showed the presence of 1.04 mmol of methyl phenylcarbamate. The TOR of the palladium was 19.4 hr$^{-1}$.

EXAMPLE 62

Acetonitrile as Solvent for Oxidative Carbonylation

Acetonitrile [25 mL], methanol [2 mL], Cu[OOCCH$_3$]$_2$ [1.2 g, 6.59 mmol] and pyridine [0.1 g, 1.27 mmol] were charged to a round bottom flask. After heating the resulting mixture to reflux, CO was passed through it at atmospheric pressure for 10 minutes Pd[OOCH$_3$]$_2$ [0.03 g, 0.134 mmol] and aniline [0.1 g, 1.08 mmol] were added and CO bubbled through for 8 minutes. An additional amount of aniline [0.1 g, 1.08 mmol] was added and CO bubbled through for another 8 minutes. The resulting solution was cooled and 0.1 g chlorobenzene added as internal standard. The solution was analyzed for methyl phenylcarbamate [2.12 mmol] and unreacted aniline [0.01 mmol]. The carbamate was formed in 98.6% yield with a TOR of 59.3 hr$^{-1}$.

EXAMPLE 63

One-Step Oxidative Carbonylation of Aniline

Acetonitrile [13.6 mL], methanol [3.4 mL], Cu[OOCCH$_3$]$_2$ [0.1 g, 0.549 mmol], pyridine [0.3 g, 3.79 mmol], Pd[OOCCH$_3$]$_2$ [0.04 g, 0.179 mmol] and aniline [0.12 g, 1.29 mmol] were charged to a quartz FP tube. The temperature was increased to 90° C. and the reaction pressure brought to 3.45 MPa (500 psi) with 3% O$_2$ in CO. The reaction time was four minutes during which the reactor was under continuous gas flow-through. Upon cooling and adding the internal standard of chlorobenzene, GC analysis indicated 0.9 mmol of methyl phenylcarbamate. The TOR of palladium was 75.5 hr$^{-1}$ while for copper it was 49.2 hr$^{-1}$.

EXAMPLE 64

Dicarbamate of Methylene Dianiline (MDA)

Acetonitrile [10 mL], toluene [10 mL], methanol [5 mL], Cu[OOCCH$_3$]$_2$ [1.6 g, 8.79 mmol] and pyridine [0.2 g, 2.53 mmol] were charged to a round bottom flask. After heating the resulting solution to reflux, CO was passed through the solution at atmospheric pressure for 10 minutes. Then Pd[OOCCH$_3$]$_2$ [0.03 g, 0.134 mmol] and methylene dianiline [0.2 g, 1.01 mmol] were added and CO bubbled through the solution for 12 minutes. The solution was cooled and thin layer chromatography did not reveal any MDA. The reaction mixture was put on a silica gel [100–200 mesh] column and eluted with 15% methanol/benzene. The dicarbamate [0.314 g, 1.00 mmol] was isolated in a 99.1% yield. The IR was identical to the product obtained from the reaction of 4.4'-methylenediphenylene diisocyanate and methanol. Melting point ranged from 174°–188° C. The MDA used in this example was derived from the condensation of formaldehyde and aniline which condensation gives a mixture of o- and p-isomers.

EXAMPLE 65

One-Step Oxidation Carbonylation of Methylene Dianiline

Acetonitrile [10.0 mL], methanol [3.0 mL], benzene [5.0 mL], Cu[OOCCH$_3$]$_2$ [0.1 g, 0.549 mmol], pyridine [0.30 g, 3.79 mmol], Pd[OOCCH$_3$]$_2$ [0.03 g, 0.134 mmol] and methylene dianiline [0.16 g, 0.808 mmol] were charged to a quartz FP tube. The temperature was increased to 100° C. and the reaction pressure brought to 3.79 MPa (550 psi) with 3% O$_2$ in CO. The reaction time was twenty-four minutes during which the reactor was under continuous gas flow-through. Upon cooling, the solution was put on a silica gel (100–200 mesh) column and eluted with 15% methanol/benzene. The dicarbamate [0.234 g, 0.745 mmol] was isolated in 92.2% yield.

The invention being claimed is:

1. A process for preparing urethane which comprises reacting a primary or secondary amine, an alcohol and carbon monoxide at a temperature of about 50° to 120° C. and a pressure of about 0.1 to 10.0 MPa and in the presence of a catalytic amount of a compound or complex of a metal selected from palladium, platinum, and rhodium and a stoichiometric amount of a copper(II) salt of a monocarboxylic acid having from 1 to 20 carbon atoms, the metal compound or complex being rhodium trichloride, platinum (II) chloride, or a compound or complex of palladium when the amine is an aromatic or aromatic heterocyclic amine; with the proviso that, when the organic moiety of the amine is substituted, the substituent is an alkyl, alkoxy, halo or aryl group and the number of substituents is 1 or 2.

2. A process according to claim 1 wherein the amine is a compound of the formula, R(NHR$^1$)n, the alcohol is a compound of the formula, R$^2$(OH)$_q$, and the copper-(II) salt of the monocarboxylic acid is a compound of the formula, Cu(O$_2$CR$^3$)$_2$, wherein: R is selected from substituted or unsubstituted C$_1$ to C$_{20}$ alkyl, alkylene, cycloalkyl, cycloalkylene, aryl, alkaryl, aralkyl, and heterocycle-containing moiety; R$^1$ is selected from hydrogen, C$_1$ to C$_6$ alkyl and C$_3$ to C$_6$ cycloalkyl; n is an integer from 1 to 4; R$^2$ is selected from substituted or unsubstituted C$_1$ to C$_{20}$ alkyl, cycloalkyl, and aralkyl; q is an integer from 1 to 3; R$^3$ is selected from substituted or unsubstituted C$_1$ to C$_{20}$ alkyl, cycloalkyl, aryl, alkaryl, and aralkyl.

3. A process according to claim 2 wherein the amine is a mono- or difunctional primary amine of up to 14 carbon atoms.

4. A process according to claim 3 wherein the amine is aniline.

5. A process according to claim 3 wherein the amine is methylene dianiline.

6. A process according to claim 2 wherein the alcohol is a monohydric alcohol of 1 to 6 carbon atoms.

7. A process according to claim 3 wherein the alcohol is selected from methanol and ethanol.

8. A process according to claim 6 wherein the alcohol is selected from methanol and ethanol.

9. A process according to claim 6 wherein the oxidant is a copper(II) salt of an aliphatic monocarboxylic acid of 1 to 6 carbon atoms.

10. A process according to claim 7 wherein the oxidant is a copper(II) salt of an aliphatic monocarboxylic acid of 1 to 6 carbon atoms.

11. A process according to claim 10 wherein the oxidant is copper(II) acetate.

12. A process according to claim 4 employing at least one Lewis base as a reaction promoter and a catalytic amount of a compound or complex of palladium.

13. A process according to claim 12 wherein the Lewis base is selected from the group aliphatic, aromatic, and heterocyclic tertiary amines and phosphines.

14. A process according to claim 3 wherein the alcohol is a monohydric alcohol of 1 to 6 carbon atoms, the oxidant is a copper(II) salt of an aliphatic monocarboxylic acid of 1 to 6 carbon atoms, the molar ratio of amine groups to metal is about 5:1 to 50:1, the molar ratio of oxidant to metal is about 2:1 to 200:1, and the catalyst turnover exceeds 2.0.

15. A process according to claim 4 wherein the alcohol is methanol or ethanol, the oxidant is copper(II) acetate, the molar ratio of amine groups to metal is 8:1 to 40:1, the molar ratio of oxidant to metal is 2:1 to 100:1, and the catalyst turnover exceeds 2.0.

16. A process according to claim 15 employing a catalytic amount of a compound or complex of palladium, and at least one Lewis base as a reaction promoter.

17. A process according to claim 16 wherein the Lewis base is selected from the group aliphatic, aromatic and heterocyclic tertiary amines and phosphines.

18. A process according to claim 17 wherein reduced copper acetate is removed from the process reactor and oxidized to regenerate copper(II) acetate.

19. A process according to claim 5 employing at least one Lewis base as a reaction promoter and a catalytic amount of a compound or complex of palladium.

20. A process according to claim 19 wherein the Lewis base is selected from the group consisting of aliphatic, aromatic, and heterocyclic tertiary amines and phosphines.

21. A process according to claim 5 wherein the alcohol is methanol or ethanol, the oxidant is copper(II) acetate, the molar ratio of amine groups to metal is 8:1 to 40:1, the molar ratio of oxidant to metal is 2:1 to 100:1, and the catalyst turnover exceeds 2.0.

22. A process according to claim 2 conducted in the presence of an additional oxidizing agent.

23. A process according to claim 1 wherein the amine is in the form of a copper carboxylate amine adduct.

24. A process according to claim 2 wherein the amine is in the form of a copper carboxylate amine adduct having the formula, [Cu(O$_2$CR$^3$)$_2$]$_m$·RNHR$^1$ wherein R, R$^1$ and R$^3$ are as defined in claim 2 and m is 0.5, 1 or 2.

25. A process according to claim 24 wherein the alcohol is a monohydric alcohol of 1 to 6 carbon atoms.

26. A process according to claim 25 wherein the oxidant is a copper(II) salt of an aliphatic monocarboxylic acid of 1 to 6 carbon atoms.

27. A process according to claim 26 wherein R$^1$ is hydrogen.

28. A process according to claim 27 wherein R$^3$ is methyl.

29. A process according to claim 28 wherein R is an alkyl group.

30. A process according to claim 29 wherein R is n-butyl.

31. A process according to claim 29 wherein R is an aryl group.

32. A process according to claim 31 wherein R is phenyl.

33. A process accordin to claim 29 wherein m is 2.

34. A process according to claim 31 wherein m is 2.

* * * * *